United States Patent [19]
Lichtman

[11] Patent Number: 5,308,357
[45] Date of Patent: May 3, 1994

[54] HANDLE MECHANISM FOR MANUAL INSTRUMENTS

[75] Inventor: Philip R. Lichtman, Newton, Mass.

[73] Assignee: Microsurge, Inc., Needham, Mass.

[21] Appl. No.: 934,002

[22] Filed: Aug. 21, 1992

[51] Int. Cl.[5] ............................................ A61B 17/42
[52] U.S. Cl. .................................. 606/205; 606/206; 606/207; 606/208
[58] Field of Search ...................... 16/110 R; 128/20; 606/170, 171, 205, 206, 207, 208

[56] References Cited

U.S. PATENT DOCUMENTS

| | | | |
|---|---|---|---|
| 1,659,112 | 2/1928 | Littlejohn | 606/205 |
| 3,750,652 | 8/1973 | Sherwin | 128/20 |
| 4,602,631 | 7/1986 | Funatsu | . |
| 5,014,407 | 5/1991 | Boughten et al. | 606/209 |

*Primary Examiner*—C. Fred Rosenbaum
*Assistant Examiner*—Noelle Kent Gring
*Attorney, Agent, or Firm*—Pandiscio & Pandiscio

[57] ABSTRACT

A surgical instrument with a scissors-type handle mechanism is provided, with the handle mechanism being characterized by first and second handle members and a toggle linkage coupled to the handle members adapted to lock the handle members in a closed position.

47 Claims, 4 Drawing Sheets

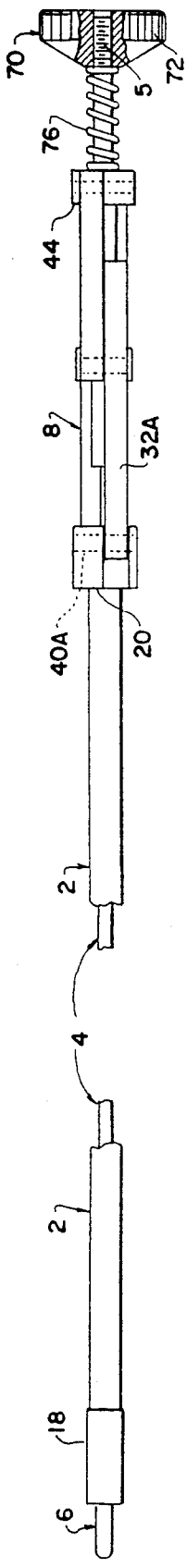
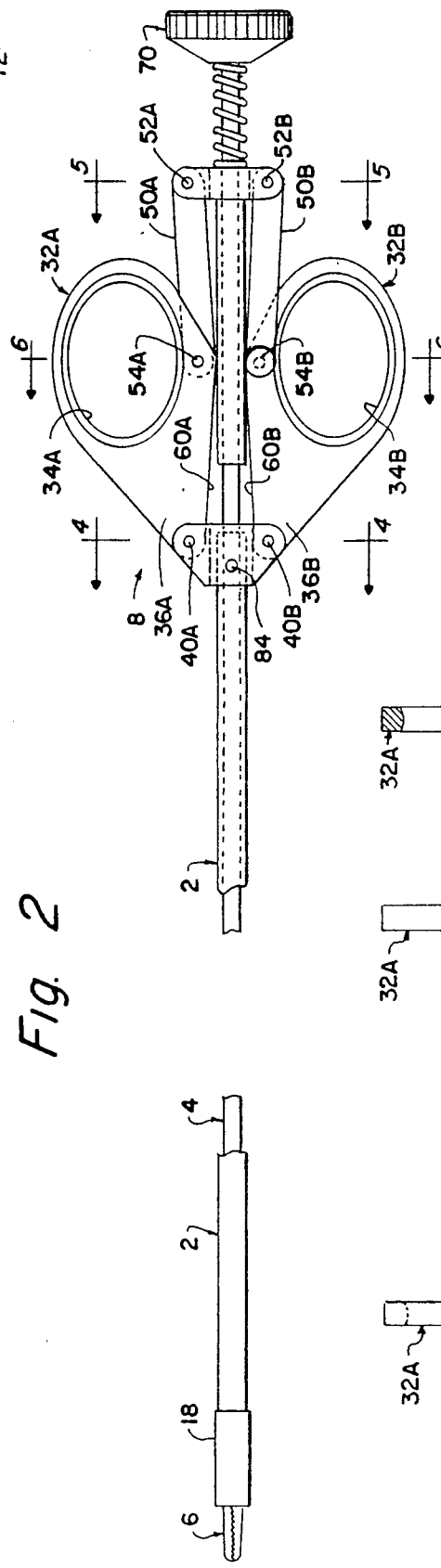
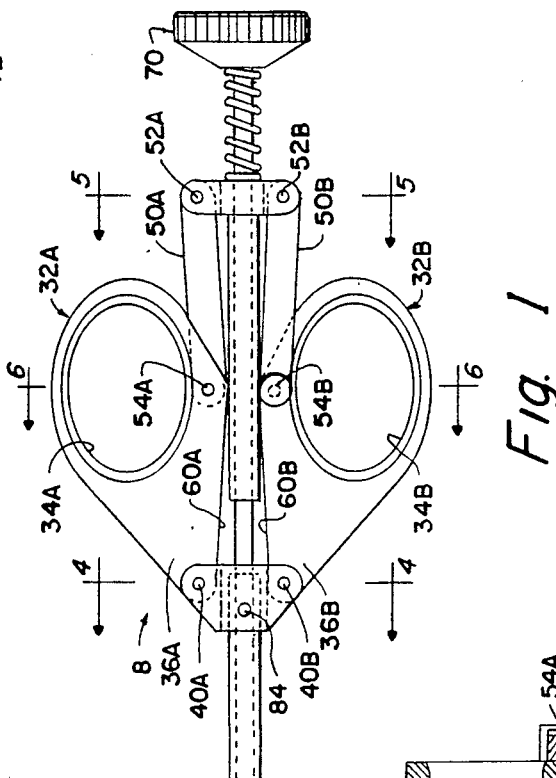
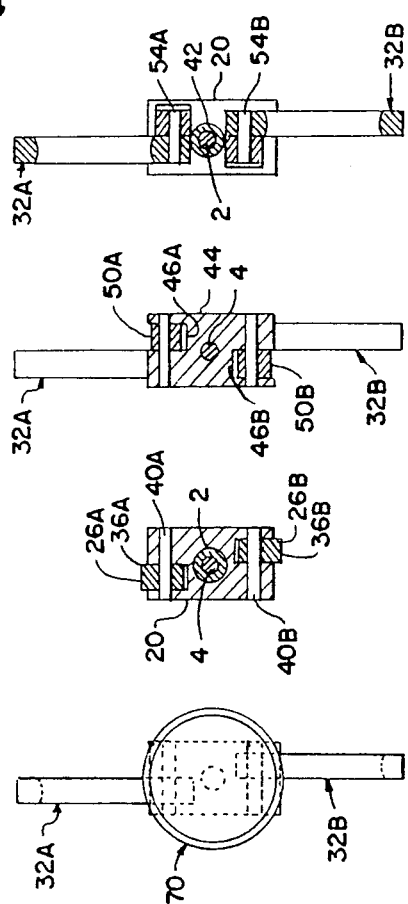
Fig. 1  Fig. 2  Fig. 3  Fig. 4  Fig. 5  Fig. 6

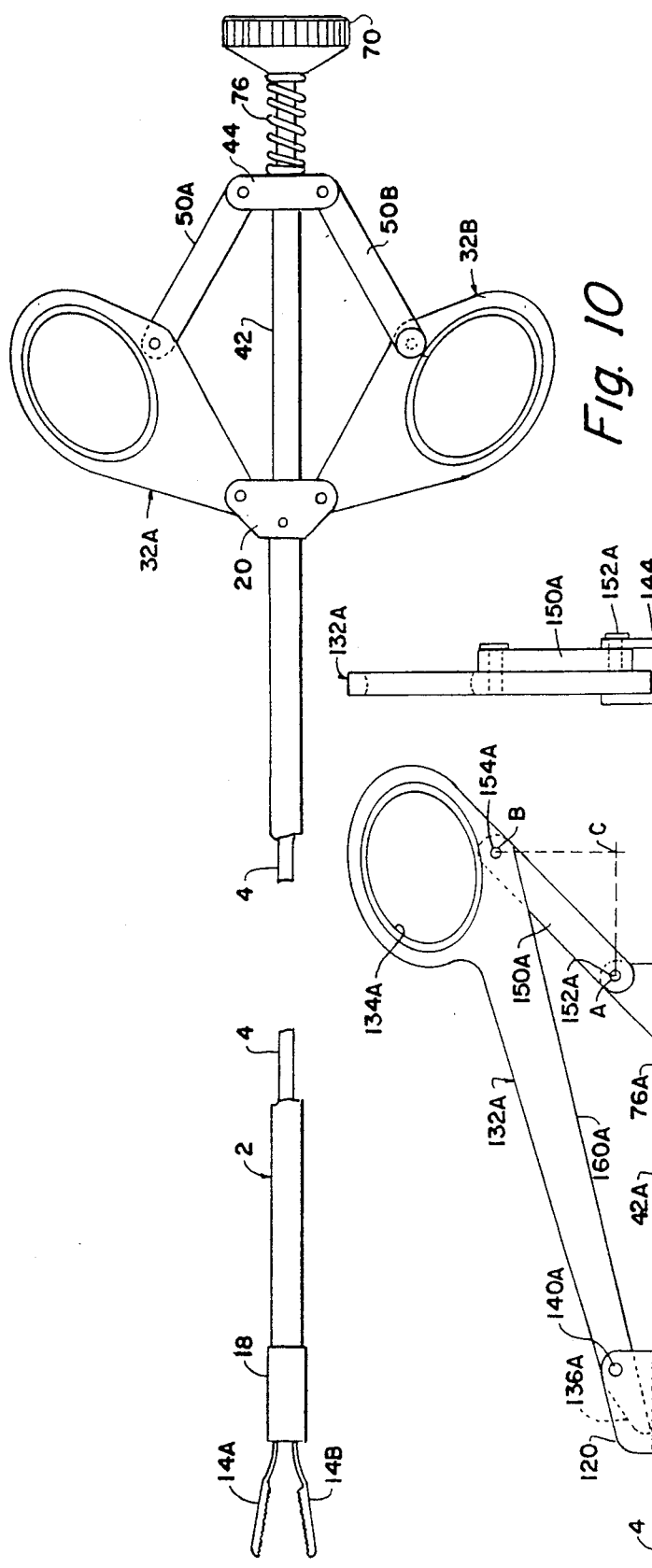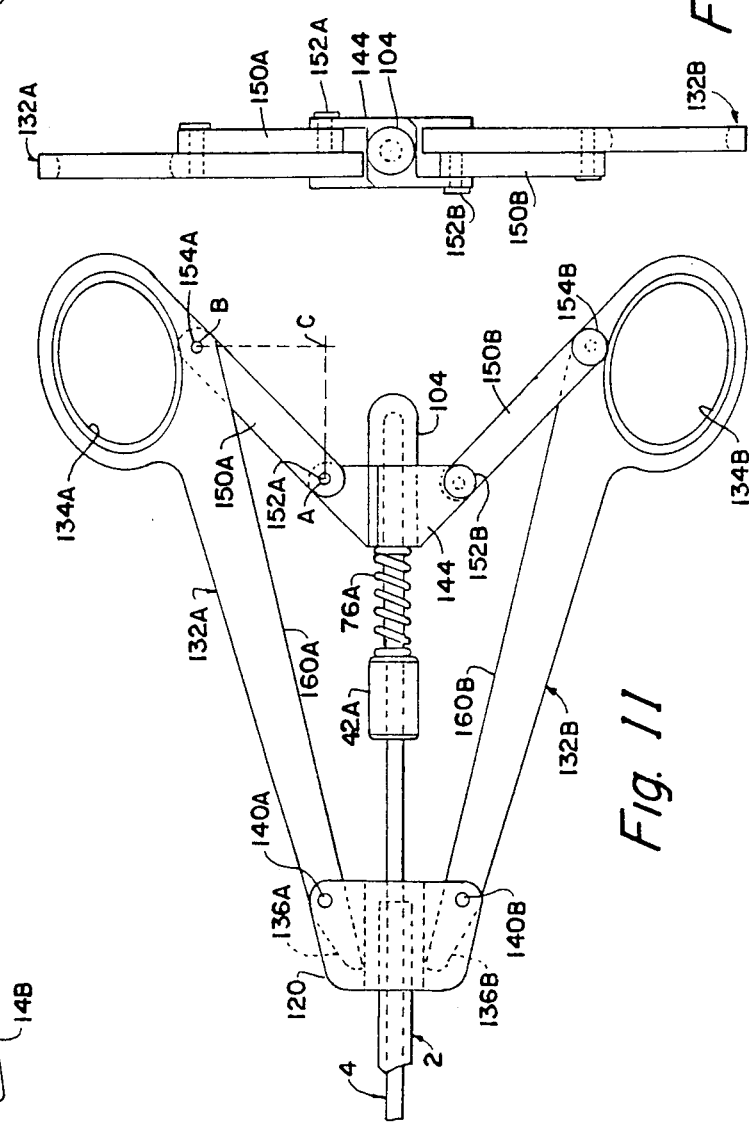

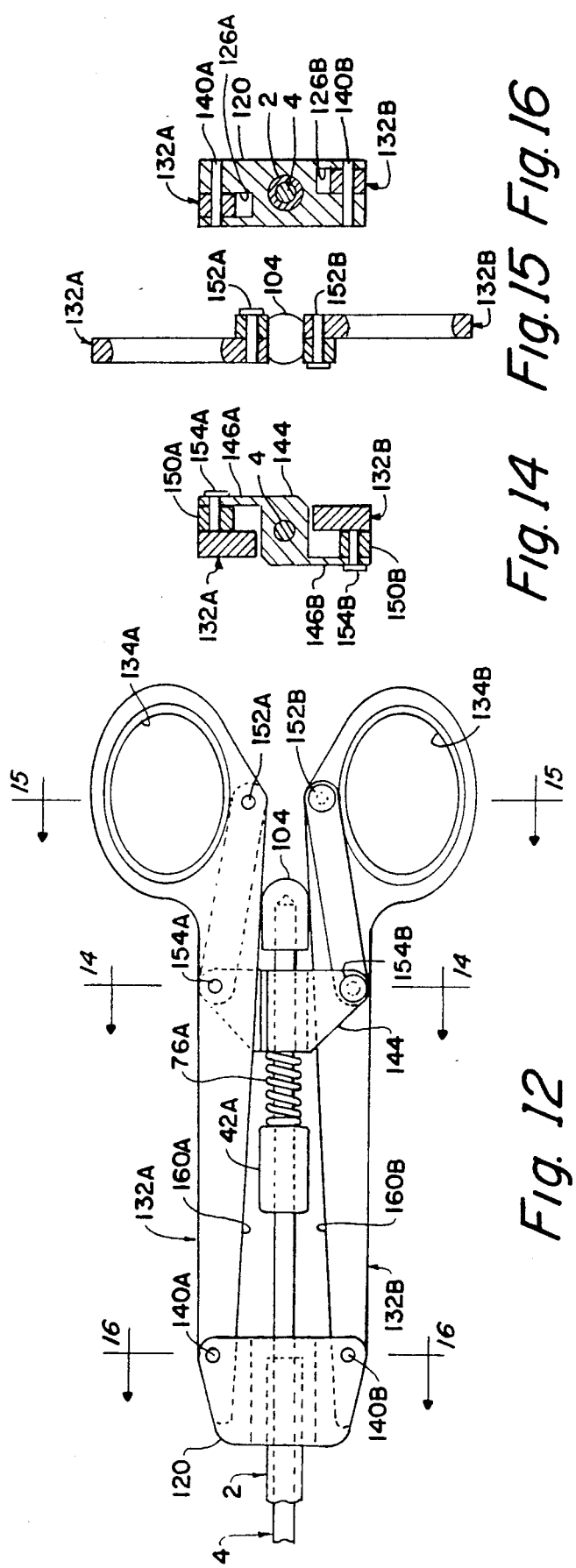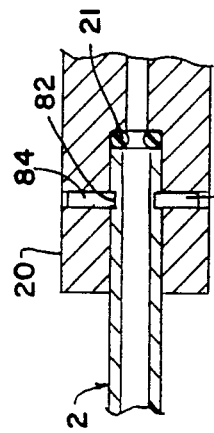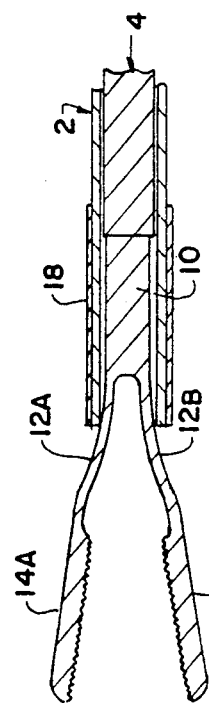

HANDLE MECHANISM FOR MANUAL INSTRUMENTS

FIELD OF THE INVENTION

This invention relates generally to surgical instruments and more particularly to surgical tools for grasping or manipulating body tissue during a surgical procedure.

BACKGROUND OF THE INVENTION

In surgical operations, it is often necessary for the surgeon to be able to grasp and/or manipulate bits of tissue precisely, particularly when the surgeon is relatively remote from the surgical site, as in performing endoscopic procedures. There are many different instruments known to persons skilled in the art for this purpose, e.g., graspers, forceps, disectors, etc. Often the grasping or manipulating is achieved by means of an instrument having a 2-part handle mechanism, a jaw mechanism comprising a pair of opposed mutually confronting jaws, and jaw supporting and operating means coupling the handle mechanism and the two jaws for causing the jaws to be moved into and out of a closed relation with one another by the surgeon's manipulation of the handle mechanism. In a typical prior art instrument, the jaw supporting and operating means comprises a relatively long hollow shaft fixed to one part of the handle mechanism, an elongated operating shaft or rod disposed for telescopic movement within and relative to the hollow shaft and adapted to cause opening and closing of the jaws according to the direction of said telescoping movement, and means connecting the rod to the other part of the handle mechanism so that telescoping movement of the rod and shaft is produced when the two parts of the handle mechanism are moved toward and away from one another. In some instrument constructions, two jaws are pivotably attached to one end of the outer shaft, and a linkage operated by the inner rod causes the jaws to be opened or closed in response to telescoping movement of the shaft and rod. In other cases the jaw mechanism comprises a pair of spring-like jaws carried entirely by the rod, with the shaft acting as a collet to force the jaws together when the telescoping movement is in one direction and release the jaws so as to allow them to open when the telescoping movement is in the reverse direction.

These and other known forms of surgical instruments designed to grasp or manipulate tissues, vessels or organs are commonly provided with some form of locking means for locking the jaws in a tissue-gripping position so that during a surgical procedure, a surgeon may let go of the instrument to attend to some other task of that same surgical procedure without fear of the instrument failing to retain its grip. Such locking means take various forms, e.g., interlocking ratchet teeth on confronting portions of a two part handle mechanism of the type where each of the two parts has a hole for accommodating a finger or thumb of the surgeon. Other types of known locking mechanisms may use a lever or a button member for engaging or disengaging the locking means.

Prior grasper-type surgical instruments are characterized by one or more limitations and disadvantages. For one thing, they are usually designed so that the force with which the surgeon can cause the instrument to grasp tissue is a function of his manual strength and the strength of the components of the instrument. Consequently the grasped tissue may be traumatized as a result of being grasped too tightly. Moreover, in the case where the jaws have teeth or serrations and/or angular rather than rounded edges, the jaws may actually sever or puncture the grasped tissue. Locking mechanisms also present disadvantages. In the case of a ratchet-type locking means, it may be necessary to deliberately warp a portion of the instrument in order to disengage the interlocking ratchet teeth. This is disadvantageous in that the force required to be applied by the surgeon to cause the required warping action may result in a reactive displacement of the instrument relative to the patient being operated, and also may require an awkward movement of the surgeon's fingers. The other types of locking mechanisms described above almost invariably require the surgeon to operate a separate control, such as a lever or button, to disengage or engage the locking mechanism. Such action by the surgeon may be inconvenient and in addition the presence of the separate control may render the instrument less comfortable to hold and maneuver.

Another disadvantage of some prior grasping instruments is that they are highly asymmetric about the longitudinal axis of the operating rod, so that it is difficult to reorient the jaws by rotating the instrument without causing an unwanted lateral excursion of the jaws. It is for this reason that many grasping-type instruments are provided with rotatable shafts and/or operating rods, plus operating means for causing such rotation. Usually this means that the surgeon must operate a wheel, knob, or other movable control member to effect the desired rotation. Depending on the nature and location of such control member, the act of reorienting the jaws can be overly distracting to the surgeon and may require the surgeon to hold the instrument in an uncomfortable or awkward manner or even require him to use a second hand to effect the rotation.

This invention results from recognition of the fact that the utility and safety of a surgical instrument intended for grasping or otherwise manipulating living tissue or a blood vessel or a human organ is diminished if the instrument lacks suitable means for limiting the clamping force exerted by the jaw and has separate controls for locking the jaws or effecting relative rotation between the jaws and the handle mechanism.

OBJECTS AND SUMMARY OF INVENTION

The primary object of this invention is to improve upon surgical instruments of the type characterized by two or more movable tissue-interacting elements, and manually operated means for moving those elements into and out of interacting relation with human or animal tissue or a blood vessel, by providing such instruments with a novel handle mechanism that is designed to limit automatically the force that can be transmitted to the tissue or vessel by the surgeon's operation of the handle mechanism.

Another object is to provide a handle mechanism for a grasper type surgical instrument that enables a surgeon to lock the instrument's jaws in gripping engagement with a blood vessel or living tissue without altering his grip on the instrument or having to operate a separate control, with the jaws remaining firmly clamped to the vessel or tissue (even if the surgeon accidently or deliberately loses contact with the instrument) until the surgeon intentionally operates the handle mechanism so as to cause the jaws to open and release the grasped vessel or tissue.

Still another object is to provide an improved scissors-type handle mechanism that is characterized by first and second handle members movable relative to one another between a first open position and a second closed position, and a toggle linkage operated by the handle members for locking the handle members in said second closed position.

A further object is to provide an improved surgical instrument of the type having a pair of jaws, a handle mechanism comprising first and second handle members movable relative to one another, and a jaw supporting and operating means connecting the jaws to the handle mechanism whereby the jaws are opened and closed by manipulation of at least one of said handle members, said jaw supporting and operating means having a hollow shaft extending between said handle mechanism and said jaws, characterized in that the handle mechanism is arranged so as to be able to effect rotation of said jaws relative to said handle mechanism about the axis of said shaft.

Another important object is to provide an improved surgical instrument of the type having an elongate hollow shaft, an operating shaft telescopingly disposed in the hollow shaft, a pair of jaws mechanically linked to one of the shafts, and a handle mechanism connected to the hollow shaft for reciprocating the inner operating shaft relative to the hollow shaft so as to cause the jaws to open or close, characterized by an improved handle mechanism that permits the surgeon to rotate the jaws relative to the handle mechanism with a comfortable and natural wrist motion, obviating the need for a separate shaft rotation mechanism and the resulting need to actuate a separate rotation control.

Yet another object of the invention is to provide a novel handle mechanism that is characterized by a pair of handles and a toggle mechanism that is coupled to the handles and is arranged to lock the handles in a selected locking position.

Still another object of the invention is to provide a novel handle mechanism that may be incorporated in a wide variety of instruments and tools that have articulating jaws.

The foregoing and other objects and advantages are achieved by a new and improved handle mechanism for use primarily in a surgical instrument of the type comprising first and second shafts disposed in coaxial telescoping relation with one another, a jaw assembly or head with at the distal (front) end of the second shaft, with the proximal (rear) end of the first shaft being attached to the novel handle mechanism that is also coupled to the second shaft, so that manipulation of the handle mechanism by the surgeon will cause the second shaft to reciprocate in the first shaft, thereby resulting in opening and closing of the jaw assembly. The novel handle mechanism of this invention is characterized by a pair of handle members, at least one of which is pivotally mounted to the proximal end of the first shaft, and a toggle linkage pivotally coupled to and extending between said one handle member and the second shaft which is described hereinafter as the operating rod. In the preferred embodiment of the invention, both handle members are pivotally attached to the proximal end of the first shaft, and pair of identical symmetrically opposed toggle linkages are connected between both handle members and the operating rod. A pre-loaded compression spring is interposed between the toggle linkages and the second shaft or operating rod so as to determine a substantially maximum force that can be transmitted between the handle mechanism and the operating rod and thereby the maximum force that is transmitted to the jaws when they are locked in closed position by manipulation of the movable handle member(s). The force that can be transmitted to the jaws, and hence to the tissue being grasped, by the operating rod coacting with the shaft is determined by the force with which the spring has been pre-loaded and the additional loading on the spring caused by the surgeon moving the handle mechanism toward the jaw locked position. In practice, the preloading of the spring is large in comparison to the amount of additional force required to compress the spring to achieve the over-center locked position. Thus, the amount of force that can be transmitted to the jaw assembly is limited to a relatively narrow range and for practical purposes forces is substantially constant. When the jaws are squeezed into clamping relation with a thick section of tissue, the spring simply compresses further so that little additional force is transmitted to the operating rod and consequently to the jaws, thus enabling the apparatus to be made relatively incapable of inflicting trauma on tissues or vessels contained between the jaws. The toggle linkage is designed so that the toggles can be driven over-center by manipulation of the two handle members, whereby any tissue captured in the jaws exerts a reaction force on the operating rod which tends to drive the toggles even more over-center, such that the apparatus is self-locking when the toggles are driven over-center. In addition the shaft and the handle mechanism can be attached to one another so as to allow the shaft to rotate on its axis relative to the handle, making it possible to reorient the jaws relative to the handle members.

Other features and advantages of the invention are illustrated in the accompanying drawings and/or described or rendered obvious by the following specific description of preferred and alternative embodiments of the invention as embodied in a surgical grasper instrument.

BRIEF DESCRIPTION OF THE DRAWINGS

FIG. 1 is a fragmentary side view in elevation of a preferred embodiment of the invention;

FIG. 2 is a plan view of the instrument shown in FIG. 1;

FIG. 3 is a rear end view looking from right to left in FIG. 1;

FIG. 4 is a cross-sectional view taken along line 4—4 in FIG. 1;

FIG. 5 is a cross-sectional view taken along line 5—5 in FIG. 1;

FIG. 6 is a cross-sectional view taken along line 6—6 in FIG. 1;

FIG. 10 is a view like FIG. 1, except that it shows the jaws and the operating handle members in fully opened position;

FIG. 11 is a fragmentary view in side elevation of a second embodiment of the invention, with the operating handle members shown in open position;

FIG. 12 illustrates the apparatus of FIG. 11 in a closed position;

FIG. 13 is an end view looking from right to left in FIG. 11;

FIG. 14 is a cross-sectional view taken along line 14 14 in FIG. 12;

FIG. 15 is a cross-sectional view taken along line 15 15 in FIG. 12; and

FIG. 16 is a cross-sectional view taken along line 16 16 in FIG. 12.

FIG. 17 illustrates a preferred form of jaw assembly;

FIG. 18 illustrates an alternative mode of attaching the instrument's shaft to the handle mechanism so as to permit relative rotation.

Like parts are identified by like numerals in the drawings.

SPECIFIC DESCRIPTION OF THE INVENTION

Figure 7:
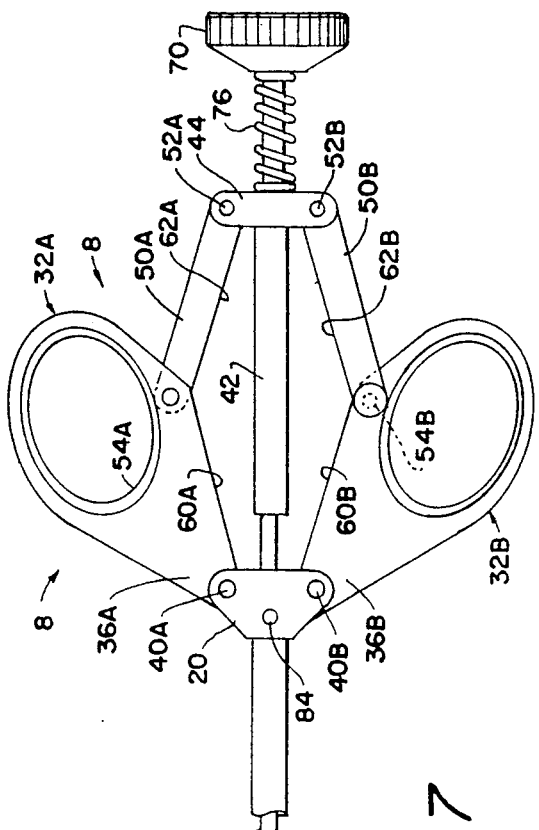
FIG. 7 is a view like FIG. 1, except that it shows the operating handle members in a partially open position, with the jaws engaged with a piece of tissue.

Referring now to FIGS. 1-10, there is shown a surgical instrument incorporating and constituting a preferred embodiment of the invention. The instrument comprises a hollow shaft 2, a close-fitting solid operating shaft or rod 4 slidably disposed in shaft 2, a jaw assembly or head 6 attached to and carried by the distal (front) end of rod 4, and a novel self-locking handle mechanism 8.

Jaw assembly 6 may take various forms. Thus, for example, it may comprise two preformed jaw members each comprising a shaped jaw and a spring-like arm having its distal end attached to the jaw in cantilever-like fashion, with the proximal ends of the two arms being anchored to the distal end of the operating rod, or else to an intermediate member that in turn is affixed to the operating rod. The two arms normally keep the two jaws in an open position wherein the jaws are spaced from one another, and the jaws are urged to closed position when the operating rod is retracted into the shaft (or, viewed another way, the shaft is moved forwardly relative to the operating rod), whereby the front end of the shaft acts as a collet, engaging the two jaw arms and forcing them and thereby the jaws together into closed position. Preferably the jaw assembly is made of a high-strength alloy, although it may be made of a plastic or composite material, and it has a one piece construction as disclosed and claimed in my copending U.S. patent application Ser. No. 07/869535, still pending, filed Apr. 15, 1992 for "Surgical Instrument For Endoscopic Surgery" (Attorney's Docket No. MICRO-1). Accordingly, to the extent not described hereinafter, the invention disclosed in my prior copending patent application Serial No. 07/869535 is incorporated herein by reference thereto.

FIG. 17 illustrates a jaw assembly or head 6 of the type described and illustrated in my copending application Ser. No. 07/869535. The jaw assembly of FIG. 17 is a one-piece unit comprising three distinct sections. A rear section 10 is secured, e.g., by welding, to the front end of operating shaft 4. Forward of rear section 58 the jaw piece is divided into two spring-like cantilever leaves or arms 12A, 12B. The forward or distal ends of leaves 12A, 12B are made thicker so as to form relatively rigid jaws 14A, 14B that have a generally rectangular configuration in cross-section (see FIG. 8). The jaws are shown as being serrated for purpose of securely grasping tissue or a vessel. However, the jaws can have other shapes, e.g., they may be smooth, tapered, grooved and/or toothed. In their unrestrained state (FIG. 17) leaves 12A, 12B diverge from rear section 10 at a substantial angle, so that there is a substantial angular gap between the jaws sufficient to admit a suitable thickness of tissue for grasping and manipulation. Leaves 12A, 12B are long enough and thick enough to be resiliently flexible over the range of motion depicted in FIGS. 1, 7, 9 and 10. The length and thickness of leaves 12A, 12B affect proper functioning of the jaw assembly. In the case of the jaw piece of FIG. 17, the leaves are not straight, but instead arc in a concave mode away from each other where they join rear section 10. However, just rearward of the junction of the leaves with jaws 14A, 14B, the leaves undergo an inflection so as to arc in a convex manner toward each other. The jaw piece 6 may be fabricated from a piece of square-section spring steel, or a steel blank of round cross-section, and it may be split into three or more jaws instead of only two jaws as shown in the drawings.

Preferably leaves 12A, 12B are sufficiently wide, as viewed normal to their thickness (see FIG. 8) to resist strongly any lateral deflection, i.e., deflection transversely to the plane of FIG. 1. The jaw piece also may be made of a suitable plastic or composite material. In the case where it is made of steel, the jaw piece is heat treated so that the leaves 12A, 12B will not deform plastically even if forced open considerably more than is shown in FIG. 10.

Shaft 4 is preferably made of metal. Shaft 2 may be made of a metal, or plastic or a composite. If shaft 2 is made of a plastic, a corrosion-resistant metal ferrule 18 may be attached to the distal or front end of that shaft as a reinforcement to prevent spreading of the relatively thin wall of the shaft under the spreading force of the jaws as operating rod 4 undergoes telescoping movement within shaft 2. Preferably shaft 2 is made of Teflon and has a square bore so as to reduce friction and minimize shaft wear by the jaws.

The proximal or rear end of shaft 2 terminates in a front pivot block 20. In the embodiment shown in FIGS. 1-10, the front pivot block 20 is rigidly secured to the rear or proximal end of shaft 2 so that it cannot move relative to the hollow shaft. However, as illustrated in FIG. 18 and described hereinafter, the front pivot block 20 may be secured to shaft 2 so as to be capable of rotating relative to the hollow shaft while being restrained against relative axial movement.

As seen in FIGS. 1 and 4-6, the front pivot block has a centrally located bore to slidably accommodate the operating rod 4 which extends rearwardly of the pivot block. Additionally the pivot block 20 has a counterbore on its front end sized to make a force fit with the rear end of shaft 2, whereby the shaft and pivot block are rendered immovable relative to one another. Preferably an 0-ring 21 is captivated between the rear end of shaft 2 and pivot block 20 as shown in FIG. 18, with the i.d. of the 0-ring as installed being such that the 0-ring makes a sliding seal with inner rod 4, thereby preventing escape of body fluids around the inner rod while allowing the latter to slide axially in outer shaft 2. Pivot block 20 is formed with two U-shaped slots 26A and 26B to accommodate two handle members 32A, 32B that form part of the handle mechanism. In the illustrated embodiment, the slots are eccentric to the center axis of the pivot block but are in opposed and parallel relation to one another. Handle members 32A and 32B are provided with finger holes 34A and 34B. In addition, the front portions of the handle members are tapered so as to have elongated, teardrop-shaped front ends 36A, 36B that extend into slots 26A and 26B. Front end sections 36A and 36B are provided with laterally-extending holes, so as to accommodate headless pivot pins 40A and 40B that extend through and are secured in aligned openings in front pivot block 20 disposed in diametrically opposed relation with shaft 2. Pivot pins 40A and 40B extend parallel to one another in a plane that extends at a right angle to shaft 2. Slots 26A and 26B are sized so that handle members 32A and 32B make close sliding fits with block 20, and thus minimize side play.

Still referring to FIGS. 1-10, the rear end of rod 4 extends through and is affixed to a spacer tube 42. Slidably and rotatably mounted on the rear end of rod 4 is a rear pivot block 44 that acts as a driver means. As seen in FIG. 5, the latter has a pair of slots 46A and 46B that are in eccentric relation to one another similar to slots 26A and 26B. Movably disposed in slots 46A and 46B are the rear or proximal ends of a pair of rear toggle links 50A and 50B. These links are pivotally secured to the rear pivot block by headless pivot pins 52A and 52B. Slots 46A and 46B are sized so that links 50A and 50B make close sliding fits therein, so as to minimize side play. The forward or distal ends of rear toggle links 50A and 50B are pivotally secured to the handle members 32A, 32B by single headed pivot pins 54A and 54B. It is to be noted that handle members 32A and 32B function as front toggle links. As seen in FIG. 6, the rear toggle links 50A and 50B extend alongside the front toggle links 32A and 32B.

Preferably, the front toggle links 32A and 32B are formed with mutually confronting edge surfaces 60A and 60B that are essentially flat, as seen in FIG. 6. Also preferably the rear toggle links 26A and 26B have mutually confronting edges surfaces 62A and 62B that are essentially flat. Additionally, it is to be noted that the distance between the two front pivot pins 40A and 40B is essentially the same as the distance between the two rear pivot pins 52A and 52B, with the distance being selected so that when the flat surfaces 60A and 60B of links 32A and 32B and/or the flat surfaces 62A and 62B of rear links 60A and 60B are moved into engagement with spacer tube 42, the center pivot pins 54A and 54B will be over-center, i.e., center toggle pin 54A will be eccentric to a straight line extending between pivot pins 40A and 52Aa, and center toggle pin 54B will be eccentric to an imaginary line extending between the front pivot pin 40B and the rear pivot pin 52B, as shown in FIG. 1.

Still referring to FIGS. 1-10, a knob 70 is affixed to the rear or proximal end of operating rod 4. Preferably, the peripheral surface of knob 70 is cylindrical and is fluted or knurled as shown at 72 so as to facilitate grasping same. Disposed on rod 4 between the rear pivot block 44 and knob 70 is a compression spring 76. The latter is sized so that it is preloaded enough to maintain rear pivot block 44 against the proximal (rear) end of spacer 42 as shown in FIG. 10.

Figure 9:
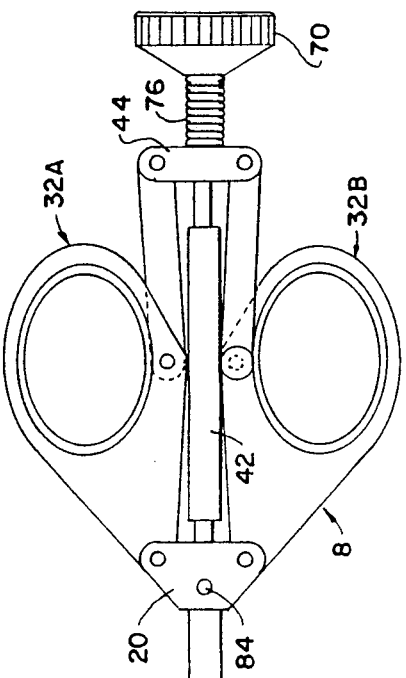
FIG. 9 is a view similar to FIG. 1 except that it shows the handle in closed relation with a piece of tissue grasped by the jaws.

FIGS. 1, 7, 9 and 10 illustrate four different positions of the handle mechanism. In FIG. 1 the handle mechanism is in closed position with the center toggle pivot pins 54A and 54B in over-center position relative to front pivot pins 40a, 40B and rear pivot pins 52A, 52B. In FIG. 10, the front toggle links 32A, 32B have been moved out to a fully open position determined by engagement of the distal (front) end of spacer 42 with front pivot block 20. In this open handle position, the jaws of the jaw assembly are in their maximum open position. FIG. 7 shows the instrument as the handle members have been squeezed toward one another far enough for the jaws to engage a section of tissue 80. FIG. 9 illustrates how, when the jaws are engaged with tissue 80, the handles can be moved to fully locked position, i.e., with pivots 54A, 54B in over center position, and in such event, the spacing between the jaws will be substantially the same as in FIG. 7 due to the force-limiting or force-compensating effect of spring 76. In this connection, it should be noted that in FIG. 9 the spring is shown compressed to a greater degree than in FIGS. 1 and 7 Movement of handle members 32a and 32B to a partially open position as shown in FIG. 7 has the effect of pulling rear pivot block 44 forward relative to operating rod 4. In FIGS. 1 and 10, compression spring 76 has its least loading, i.e., it is in its preloaded condition, due to the fact that the jaws are not grasping any tissue.

The front links 32A and 32B and the rear links 50A and 50B form a parallelogram linkage consisting of two like toggles. As a result, when the front links 32A and 32B are manipulated by the user, the pivot blocks 20 and 44 are caused to move closer to, or further apart from, each other along the axis of hollow shaft 2 and operating rod 4, resulting in the rod being moved rearward so as to retract its front end into hollow shaft 2 so as to cause the jaw assembly to close (FIG. 1), or move forward relative to the shaft 2 so as to allow the jaws of the jaw assembly to open (as shown in FIG. 10).

It is to be appreciated that the force with which the operating rod 4 undergoes reciprocation inside the hollow shaft is limited to the force at which the compression spring 76 has been pre-loaded, plus any additional force exerted to compress the spring further. This is best understood by a description of operation of the instrument shown in FIGS. 1-10 in relation to the grasping of a piece of tissue 80. In FIG. 10, the jaws 14A and 14B of the jaw assembly are in fully open position due to the fact that handle members 32A and 32B (the front links of the toggle mechanism) have been moved to fully open position. At this point, the position of the operating rod 4 relative to the shaft 2 is determined by engagement of spacer 42 with pivot block 44.

Figure 8:
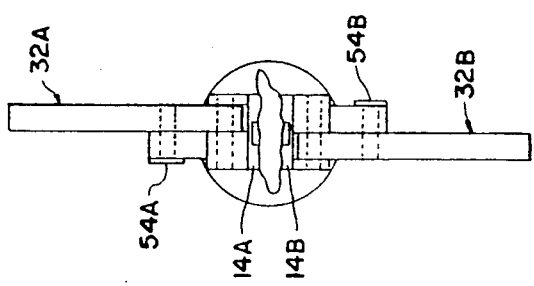
FIG. 8 is an end view of the jaws of the instrument as shown in FIG. 7.

If jaws 14A and 14B do not embrace any tissue, when front links 32A and 32B are moved toward one another from the position of FIG. 10 to the position of FIG. 1, the rear pivot block 44 will move rearward away from front pivot block 20 and push on the preloaded compression spring 76, with the force being transmitted through the spring to the knob 76. Since the knob is rigidly attached to operating rod 4, the latter will move rearward with respect to front pivot block 20 and hollow shaft 2, causing the jaws to close. However, if an object, such as a piece of tissue 80 as shown in FIGS. 7-9, is positioned between the jaws, and if the front links 32A, 32B are progressively brought together, i.e., moved from the position of FIG. 10 through the position of FIG. 7 toward the position of FIG. 9, then at some point the resistance exerted by the tissue against the jaws becomes sufficiently great to overcome the preload of spring 76. Consequently, further closing movement of the front handle links 32A and 32B will have little closing effect on the jaws, with the compression spring 76 compressing further so as to permit the jaws to continue to hold the tissue with an almost constant force even though the front links 32A and 32B are further drawn together until they are in the over-center locked position (FIG. 9). Hence traumatization of the tissue is minimized. Engagement of surfaces 60A, 60B and/or 62A, 62B with spacer sleeve 42 acts to determine the maximum closed position of handle links 32A and 32B. In this state, as seen in FIGS. 1 and 9, the pivots 54A, 54B of front links 32A and 32B have progressed across the imaginary lines running from front pivot pins 40A, 40B to rear pivot pins 52A, 52B. Spring 76 then acts to urge the toggle links to remain in their over center positions with spacer tube 42 acting as a stop. When it is desired to release tissue 80, the front handle links 32A and 32B must be drawn apart deliberately by the user far enough to release the toggle mechanisms from their locked state. This toggle locking action is advantageous since when the toggles are in their locked over-center position, the surgeon may let go of the instrument without affecting the tenacity with which the living tissue is held by the jaws. The angle of the jaws when in gripping relation with tissue or a blood vessel or an organ depends on the amount or size of the tissue, vessel or organ. However, both the locking and the force-limiting features of the instrument apply regardless of the angle of the jaws when in grasping relation with tissue, or another object.

Having the operating knob 70 affixed to the operating rod 4 offers the advantage that when a piece of tissue as shown at 80 is captured by the jaws, instantaneous release of the tissue can be achieved by having the surgeon press axially on knob 70 while holding the rest of the instrument against movement. Also, when the instrument is left in its locked state with tissue 80 grasped by the jaws, the grid exerted on the tissue can be lessened so as to permit manipulation of the jaws relative to the tissue by first pressing and then releasing knob 70, since the spring 76 provides a restoring force that tends to close the jaws when the knob is no longer depressed. Preferably, spring 76 has a free length (i.e., a length in its uncompressed state) that is substantially greater than its initial preloaded length, so that the force it exerts between knob 70 and rear pivot block 44 varies relatively little over the operating range of motion of the parts. A further advantage of knob 70 is that the apparatus may be positioned or manipulated by grasping the knob alone, an advantage made possible because knob 70 may be made in a relatively small size and conveniently contoured for manual grasping, and also because of the maximally long maneuvering radius of the instrument when it is held by the knob and pivoted about the cannula with which it may be introduced into the surgical cavity. This mode of manipulating the apparatus affords a fine degree of control when positioning jaws 14A and 14B in the surgical area or when it is desired to withdraw tissue that has been secured by the jaws.

A further advantage is attainable if the hollow shaft 2 is not locked against rotation relative to front pivot block 20. As shown in FIG. 18, the rear or proximal end of shaft 2 may be formed with a circumferential groove 82 that is engaged by one or more retaining pins 84 received in pivot block 20. The pin(s) 84 prevent axial movement of shaft 2 relative to block 20, while permitting the shaft to rotate on its axis relative to the block.

If desired, as shown in FIG. 2, the proximal end of rod 4 may have a screw thread 5 and knob 70 may have a through hole that is threaded to mate with the screw thread on the rod. In su--h case, relative rotation of the knob will cause it to move axially along the rod and thereby alter the preloading of spring 76.

FIGS. 11-6 illustrate a second embodiment of the invention which differs from the device of FIGS. 1-10 with respect to the direction of motion of the operating rod relative to the hollow shaft in response to movement of the articulated handle toggle linkage. In this embodiment the operating rod 4 and the hollow shaft 2 are essentially the same as in the embodiment shown in FIGS. 1-10, with the exception that the spacer sleeve 42 is replaced by a short length collar 42A that is affixed to the operating rod. In addition, the proximal end of the operating rod has a cap 104 affixed thereto. As seen in FIGS. 12 and 16, the front pivot block 120 is generally similar in shape to the front pivot block 20, with the block having a close fitting bore to slidably accommodate the operating rod and a counterbore in which the hollow shaft 2 is affixed, preferably by a force-fit, or alternatively by brazing or welding or a suitable cement. Pivot block 144 has an axial bore sized to make a close sliding fit with operating rod 4. Block 144 and a compression spring 76A are captured in the order named between cap 104 and collar 42A. Spring 76A urges the rear pivot block away from collar 42A toward cap 104.

Referring now to FIGS. 14-16, front pivot block 120 is provided with slots 126A, 126B similar to the slots 26A, 26B in front pivot block 20, while rear pivot block 144 has offset parallel projections 146A and 146B. In this case the front handle toggle links 132A and 132B are longer than the corresponding links 32A and 32B, and are secured to the front pivot block 120 by corresponding like pivot pins 140A and 140B. Handle members 132A and 132B have holes 134A, 134B to accommodate the surgeon's thumb and forefinger. Single head pivot pins 152A and 152B are used to secure the front (distal) ends of rear toggle links 150A, 150B to the projections 146A and 146B respectively of rear pivot block 144. The rear ends of links 150A, 150B are pivotally coupled to the front links 132A and 132B by single head pivot pins 154A and 154B.

The front end of shaft 2 and operating rod 4 are essentially as shown in FIGS. 1-10, with the front end of the shaft acting as a collet for a jaw piece as shown at 6 in FIG. 1. The front links have flat mutually confronting surfaces 160A and 160B and have front tip portions 136A, 136B (FIG. 11) that engage the bottoms of slots 126A, 126B to limit outward pivoting movement of the handles to jaw opening position.

Assuming that the jaw assembly used with the embodiment shown in FIGS. 11-6 is the same as the one shown in FIGS. 1-10, operation of the second alternative embodiment is essentially as follows. When the front links 132A, 132B are moved toward one another, they can be moved to an over-center locking position wherein their flat surfaces 160A and 160B engage cap 104 and the rear pivot pins 152A and 152B are in over-center position (FIG. 12). When the front links are urged apart by the surgeon whose fingers are inserted in the finger holes 134A and 134B, the rear ends of rear links 150A and 150B move outward along a line substantially perpendicular to the axis of hollow shaft 2. In this connection it should be noted that although in fact the movement is a circular arc, the radius of the arc, which is nearly the entire length of the front links 132A, 132B, is sufficiently long as to be, over a limited range of motion and only for practical purposes, infinite. As seen in FIG. 11, when the handle mechanism is moved to the open position, rear links 150A and 150B are seen to constitute one side of a triangle delineated by points ABC. If the approximation is made that the front links 132A, 132B are infinitely long for practical purposes as elaborated above, then the triangle ABC is a right triangle and the rear link 150A is its hypotenuse. Consequently, if the front link 132A is pivoted about the axis of pivot pin 140A, the rear pivot block 144 necessarily slides axially along the operating rod 4.

Because of the shouldered cap 104 on the rear (proximal) end of the rod 4, rearward movement of rear pivot block 144 results in a corresponding rearward movement of the operating rod 4. The front face of the rear pivot block abuts the compression spring 76A, which in turn abuts the collar 42A that is affixed to operating rod 4. This arrangement, which is conceptually the same as that of the preferred embodiment shown in FIGS. 1–10, has the same beneficial effect of limited force transmission of the jaws and of automatic locking of the handle when the links are drawn into their closed, over-center attitude as shown in FIG. 12.

It is to be appreciated that in both of the embodiments illustrated in the drawings, the limited forces that can be imposed on the jaws may be made adjustable with little increase in complexity of the instrument. Thus, as illustrated in FIG. 2, the preferred embodiment of FIGS. 1–10 could be modified by arranging for the knob 70 to be screwed onto a threaded portion 5 (FIG. 2) of the operating rod 4, so that when the knob is rotated, it will move along the operating rod 4, and thereby adjust the preload compression of spring 76.

In the case of the second embodiment shown in FIGS. 11–16, the amount of preloading of spring 76A can be varied if the collar 42A is made so that it has an internal screw thread that is mated with a threaded portion of operating rod 4, so that rotating the collar on the operating rod will shift its axial position on the rod, with the result that the preloading of the spring can be adjusted.

It is believed to be obvious from the drawings that the embodiment of FIGS. 11–16 has the advantage that no portion of the apparatus extends rearwardly beyond the rearmost links of the handle mechanism, thereby providing the apparatus with a visually appealing appearance and also eliminating the presence of any mechanism in the region of the user's palm. However, the second embodiment tends to provide a lesser overall stroke, i.e., length of travel, of the operating rod as compared with that of the preferred embodiment of FIGS. 1–10 (assuming that the general dimensions of the two embodiments are essentially equivalent or equal).

The arrangement shown in FIG. 18 allows the front pivot block 20 to rotate relative to the hollow shaft 2, while preventing relative axial motion between those components. This has the advantage that when the jaws are engaged with a piece of tissue, the surgeon may rotate the handle mechanism without altering the position of the jaws. Alternatively the surgeon may rotate the jaws by manipulating the knob 70, without causing likewise rotation of the handle assembly. Consequently, the surgeon has the option of positioning the jaws in a manner most suited to his task, while permitting the handle assembly to be located in an orientation that is most comfortable or convenient for the surgeon. An important safety feature of the two embodiments shown in the drawings is that the jaws will not open if one of the two operating handle members (32A or 32B, or 132A or 132B) is accidentally urged to open position, since the other toggle linkage comprising the other opposite handle member will resist the unlocking action.

Obviously there are many ways to construct and utilize toggle linkages arranged to cause relative reciprocation between coaxial shafts. Similarly, other jaw assemblies may be used in place of the jaw assembly shown in the drawings. Thus, for example, a jaw assembly may be used that comprises (1) two separately-formed jaw members that are attached to the outer shaft, with one jaw member being pivotally mounted relative to the other, and (2) means coupling that one jaw and the inner shaft for causing opening and closing movement of the jaws in response to relative telescoping movement of the outer and inner shafts.

Similarly, although the drawings show symmetrically oppositely-disposed pairs of toggle links, it is recognized that only one toggle may suffice, since the second toggle is kinematically redundant and serves primarily to confer symmetry (for ease of handling) and also to minimize bending moments in the outer and inner shaft for the purpose of minimizing the size and weight of the components. Consequently, an embodiment utilizing only a single toggle mechanism is considered to be within the scope of this invention. Thus, for example, in the preferred embodiment, the links 32B and 50B may be eliminated; similarly the second embodiment may be made to function without links 132B and 150B. In the case of such elimination, a handle member or finger loop means is affixed to the front pivot block for engagement by a finger of the surgeon, with that handle member or loop being located somewhere between the front and rear pivot blocks in the preferred embodiment and somewhere rearward of the rear pivot block in the embodiment of FIGS. 11–16.

It is to be appreciated also that more than two jaws and more than two toggle arrangements may be used. If, for example, in the preferred embodiment three to six jaws and toggles were to be disposed symmetrically about the axis of hollow shaft 2 and operating rod 4, it would be possible to embrace or encompass those toggles with an elastomeric skin, such as a rubber bulb, so that the user could, by way of squeezing the bulb, urge the toggles to their closed position, to close the instrument's jaws, thereby eliminating the need for the finger holes 34, 34B and 134A, 134B. The jaws would be opened by pushing forward knob 70.

The slots 26A, 26B and 46a, 46B need not be eccentric, i.e., laterally displaced from one another as shown in FIGS. 4 and 5, but instead may be co-planar, in which case links 50A, 50B are made relatively thin and are received in center slots in handle members 32A and 32B. In such case it is preferred that all of the pivot pins are headless.

It is also considered that although the toggles as described and illustrated are articulated linkages, it may be possible to combine the front and rear linkages of each toggle mechanism into a single strip of spring-like material such as spring steel, which would arc convexly away from the shaft when the jaws are opened, but which when squeezed beyond parallelism with the shaft, would snap over-center in a concave shape and lock the apparatus in the manner similar to that achieved by the embodiment shown in the drawings.

Other possible modifications include replacing solid shaft or rod 4 with a hollow shaft, and providing the tool with an electrical terminal or terminals so that it may be electrified in a monopolar or bipolar fashion for cauterization purposes. Also it is possible to modify the jaws so as to incorporate a cutter blade in one and a blade-receiving groove in the other, whereby to sever tissue or a vessel gripped by the jaws. Such a grasper/cutter combination is shown in my copending U.S. application Serial No. 07/809535 cited supra.

Finally, it is to be appreciated that although the instrument herein described and illustrated is designed for surgical procedures, the invention is applicable to the provision of manually operated instruments and tools for purposes other than surgical procedures.

What is claimed is:

1. A surgical instrument comprising:
    an outer, hollow shaft having a longitudinal axis, a first proximal end, a first distal end and a first length;
    an inner shaft co-axially disposed in said outer shaft for reciprocal movement with respect to said outer shaft, said inner shaft having a second proximal end, a second distal end, and a second length, said second length being longer than said first length;
    means for surgical interaction with animal tissue associated with said first and second distal ends, said surgical interaction means comprising first and second tissue interacting means movable relative to one another transversely of said longitudinal axis between a first open position and a second closed position by axially directed changes in the relative positions of said first and said second distal ends; and
    a self-locking mechanism for changing the relative positions of said first and said second distal ends lengthwise of said longitudinal axis, said mechanism comprising:
    (A) driver means mounted on said inner shaft substantially adjacent said second proximal end, said driver means being slidable relative to said inner shaft along the axis of said inner shaft;
    (B) at least one flexible linkage means having a first linkage end, a second linkage end and a central portion, said first linkage end being connected to said outer shaft at a first point located radially outwardly of and substantially adjacent to said first proximal end of said outer shaft, said second linkage end being connected to said driver means at a second point located radially outwardly of said inner shaft, and said central portion being adapted to receive a force applied substantially normally to said longitudinal axis and transmit said force to said driver means and said outer shaft so as to move said driver means relative to said outer shaft along the axis of said inner shaft, the maximum length of said linkage means being longer than the minimum axial separation between said first point and said second point when said first and second tissue interacting means are in said first open position and also when said first and second tissue interacting means are in said second closed position; and
    (C) force-transmitting means coupled to said inner shaft and engageable by said driver means for transmitting an axial force from said driver means to said inner shaft in response to a force applied to said central portion normally of said longitudinal axis, whereby a force applied to said central portion in a first direction normal to said longitudinal axis will cause said linkage to move said driver means in a first axial direction and a force applied to said central portion in a second opposite direction normal to said longitudinal axis will cause said linkage to move said driver means in a second opposite axial direction, whereby said first and second tissue interacting means are caused to move from one to the other of said first open position and said second closed position depending on the direction of the normal force applied to said central portion;
    said linkage being arranged so as that said mechanism is self-locking when said first and second tissue interacting means are in said second closed position.

2. An instrument according to claim 1 wherein said linkage is arranged so that said mechanism is self-locking when said first and second interlocking means are in grasping relation with tissue.

3. An instrument according to claim 1 wherein said force-transmitting means comprises biasing means on said inner shaft urging said driver means toward said distal end of said inner shaft;

4. An instrument according to claim 3 wherein said biasing means is a compression spring surrounding said inner shaft, and further wherein said force-transmitting means comprises a shoulder on said inner shaft, with said spring being captivated between and compressed to a selected loading by said shoulder and said driver means.

5. An instrument according t claim 4 further including means for adjusting the pre-loading of said spring.

6. An instrument according to claim 5 wherein when said first and second tissue interacting means are in said second closed position or interacting with tissue, forces applied to said driver means by said linkage means in said first axial direction which are larger than the pre-loading on said spring will cause said driver means to move along said inner shaft in said first axial direction so as to compress said spring, whereby substantially no further closing force is applied to said first and second tissue interacting means.

7. An instrument according to claim 1 wherein said linkage is a toggle linkage having a center pivot, and further wherein said tissue interacting means may be locked in their second closed position by forcing said center pivot of said linkage means toward said longitudinal axis far enough to pass through a line extending between the points of connection of said linkage to said driver means and said outer shaft.

8. A surgical instrument according to claim 1 characterized by means associated with said inner shaft for limiting movement of said driver means along said inner shaft in a second direction opposite to said first direction, whereby forces applied to said driver means by said linkage means in said second direction will cause movement of said inner shaft in said second axial direction relative to said outer shaft thereby moving said tissue interacting means toward said open position.

9. A surgical instrument according to claim 1 having a plurality of said linkage means disposed in equally spaced circumferential relation to each other about said coaxial shafts.

10. A surgical instrument according to claim 3 wherein said biasing means comprises a helical compression spring having a first end and a second end surrounding said inner shaft between said driver means and said second proximal end of said inner shaft, and a member on said second proximal end of said inner shaft engaged with said second end of said spring, said member being positioned so as to urge said driver means toward said distal end of said inner shaft.

11. A surgical instrument according to claim 1 having movement-limiting means on said inner shaft for limiting movement of said inner shaft relative to said outer shaft in a selected axial direction.

12. A surgical instrument according to claim 12 wherein said movement-limiting means comprises a cap attached to said second proximal end of said inner shaft, and further wherein said force-transmitting means comprises a spring on said inner shaft urging said driver means toward said cap.

13. A surgical instrument according to claim 1 wherein said linkage is a toggle linkage comprising first and second links, first pivot means pivotally connecting one of said first link to said proximal end of said outer shaft, second pivot means pivotally connecting one end of said second link to said driver means, and a third pivot means pivotally connecting the other end of said second link to said first link at a point spaced from said one end of said first link.

14. A surgical instrument according to claim 13 wherein said toggle linkage is arranged so that the pivot point of said third pivot means can be moved to an over-center position with respect to the pivot point of said first member and said outer shaft and the pivot point of said second member and said driver means.

15. A surgical instrument according to claim 13 having two identical toggle linkages arranged in diametrically opposed relation with one another about said longitudinal axis, each of said toggle linkages being arranged so that the pivot point of its said third pivot means can be moved to an over-center position with respect to the pivot point of its said first member and said outer shaft and the pivot point of its said second member and said driver means.

16. A surgical instrument according to claim 13 wherein each of said first members is arranged with a hole for accommodating a surgeon's finger or thumb.

17. A surgical instrument according to claim 16 wherein said first and second interacting members are jaws adapted to grip tissue therebetween.

18. A surgical instrument according to claim 1 wherein said inner shaft is rotatable on its axis relative to said outer shaft and said driver means.

19. A surgical instrument comprising:
- a hollow outer shaft having a proximal end and a distal end;
- an inner shaft having a proximal end and a distal end, said inner shaft being located within said outer shaft and being movable bidirectionally along the axis of said outer shaft;
- tissue-interacting means for interacting with tissue associated wit said first and second distal ends, said tissue-interacting means being movable between an open position and a closed position in response to changes in the relative positions of said first and said second distal ends lengthwise of the axes of said shafts caused by telescoping movement of said outer and inner shafts;
- a mechanism for effecting said telescoping movement and controlling said relative positions of said first and second distal ends along said axes, said mechanism comprising:
  first pivot block means attached to said outer shaft adjacent the proximal end of said outer shaft;
  second pivot block means slidably mounted on said inner shaft substantially adjacent said proximal end of said inner shaft;
  spring means on said inner shaft, said spring means bearing against said second pivot block means so as to inhibit movement of said second pivot block means along said inner shaft in a first axial direction, said first axial direction being selected such that movement of said inner shaft in said first axial direction relative to said outer shaft will move said tissue-interacting means toward said closed position;
  toggle linkage means connecting said first and second pivot block means, said linkage means including a first link having a first end pivoted to said first pivot block means and a second end adapted to be gripped for application of a manual force, said second link including a first end pivoted to said first link and a second end pivoted to said second pivot block means;
  whereby (1) forces applied by said linkage means to said second pivot block means in said first axial direction will cause relative movement of said inner shaft in said first axial direction tissue-interacting means towards said closed position, (2) when said tissue-interacting means is in said closed position or interacting with tissue, forces applied to said driver means by said linkage means in said first axial direction which are larger than a predetermined maximum axial force in said first axial direction will cause said second pivot block means to slide along said inner shaft in said first axial direction.

20. An instrument according to claim 19 wherein said toggle linkage is adapted to lock said tissue-interacting means in said closed position.

21. A surgical instrument according to claim 20 further having mans on said inner shaft for limiting axial movement of said inner shaft relative to said outer shaft.

22. In a surgical instrument of the type including a first shaft reciprocally disposed within a second shaft and first and second tissue-interacting means associated with one end of said shafts, said tissue-interacting means being movable relative to one another between an open position and a closed position in response to relative telescoping movement of said first and second shafts, and means for causing relative telescoping axial movement between said shafts, the improvement comprising:
- a self-locking mechanism for effecting and controlling relative axial movement between said shafts, said mechanism being associated with the other ends of said shafts and including a first pivot block, a second pivot block, biasing means, and toggle linkage means connecting said first and second pivot blocks;
- said first pivot block being secured to said second shaft and said second pivot block being slidably mounted on said first shaft, said biasing means being coupled to said first shaft and bearing against said second pivot block so as to inhibit movement of said second pivot block along said first shaft in a first direction, said first direction being selected to correspond to the direction of axial movement of said first shaft relative to said second shaft which tends to close said first and second tissue-interacting means, and said toggle linkage means comprising first and second links, said first link connected at one end to said first pivot block, and said second link connected at one end to said second pivot block and at its opposite end to said first link, said first link having its opposite end adapted for grasping by a surgeon, said toggle linkage means having a maximum length longer than the minimum distance between said first pivot block and said second pivot block when said first and second tissue-interacting means are in said closed position, such that said linkage means normally is angulated outwardly away from said first shaft but may be made to angulate inwardly toward said first shaft far enough to lock said first and second tissue-interacting means in said closed position.

23. An instrument of the type having first and second shafts disposed in telescoping relation with one another, an articulating assembly carried by at least one of said shafts, said assembly comprising at least first and second tissue-interacting members and means responsive to telescoping movement of said first and second shafts for causing said tissue-interacting members to move into closing relation with one another when said first and second shafts undergo telescoping movement in a first direction and into opening relation with one another when said first and second shafts undergo telescoping movement in a second opposite direction, and an operating mechanism connected to said first and second shafts for selectively causing said first and second shafts to undergo telescoping movement in said first or second direction and for locking said shafts against relative movement when said tissue-interacting members are in closed relation with one another, said operating mechanism being characterized by at least first and second toggle links, said first toggle link being pivotally coupled at a first point to one end of said first shaft and at a second point spaced from said first point to a first end of said second toggle link, and said second toggle link being pivotally coupled at a second opposite end to said second shaft, said toggle links being arranged relative to said first and second shafts so that said links can be moved between a first over-center toggle position wherein said first and second shafts are locked against telescoping movement in a first telescoped state and a second toggle position wherein said first and second shafts are in a second telescoped state, said shafts being positioned to hold said tissue-interacting members in closed relation with one another when said toggle links are in said first over-center position and said first and second shafts are in said first telescoped state.

24. An instrument according to claim 23 wherein said second toggle link is coupled to said second shaft indirectly via a pivot block slidably mounted on said second shaft, and further wherein a spring is mounted on said second shaft so as to preload said pivot block on said second shaft.

25. An instrument according to claim 24 adapted for surgical procedures, characterized in that said first toggle link has a finger hole for accommodating a finger of a surgeon.

26. An instrument according to claim 24 wherein said mechanism comprises a second pair of first and second toggle links coupled and arranged like said first-mentioned first and second toggle links.

27. An instrument according to claim 26 wherein said second pair of toggle links are disposed in diametrically opposed relation to said first-mentioned first and second toggle links.

28. An instrument according to claim 27 wherein each of said first toggle links has an opening for accommodating a finger or thumb of a surgeon.

29. An instrument according to claim 28 wherein said tissue-interacting members are jaws.

30. A surgical instrument according to claim 1 wherein said surgical interaction means comprises first and second members each having a distal end and a proximal end, and means connecting the proximate ends of said first and second members to the distal end of said inner shaft, whereby relative axial movement of said inner and outer shafts in one direction will cause the distal end of said outer shaft to force said first and second members to move from said first open position to said second closed position, and relative axial movement of said inner and outer shafts in the opposite direction will cause said first and second members to move from said second closed position to said first open position.

31. A surgical instrument according to claim 1 wherein said driver means is always spaced axially from the second proximal end of said inner shaft.

32. A surgical instrument comprising:
an outer, hollow shaft having a longitudinal axis, a first proximal end, a first distal end and a first length;
an inner shaft co-axially disposed in said outer shaft for reciprocal movement with respect to said outer shaft, said inner shaft having a second proximal end, a second distal end, and a second length, said second length being longer than said first length;
means for surgical interaction with animal tissue associated with said first and second distal ends, said surgical interaction means comprising first and second tissue interacting means movable relative to one another transversely of said longitudinal axis between a first open position and a second closed position by axially directed changes in the relative positions of said first and second distal ends; and
a self-locking mechanism for changing the relative positions of said first and said second distal ends lengthwise of said longitudinal axis, said mechanism comprising:
(A) driver means slidably mounted on said inner shaft;
(B) at least one flexible linkage means having a first linkage end, a second linkage end and a central portion, said first linkage end being connected to said outer shaft at a first point located radially outwardly of and substantially adjacent to said first proximal end of said outer shaft, said second linkage end being connected to said driver means at a second point located radially outwardly of said inner shaft, and said central portion being adapted to receive a force applied substantially normally to said longitudinal axis and transmit said force to said driver means and said outer shaft so as to urge said driver means to move relative to said outer shaft along the direction of the axis of said inner shaft, the maximum length of said linkage means being longer than the minimum axial separation between said first point and said second point when said first and second tissue interacting means are in said first open position and also when said first and second tissue interacting means are in said second closed position; and
(C) force-transmitting means coupled to said inner shaft and engageable by said driver means for transmitting an axial force from said driver means to said inner shaft in response to a force applied to said central portion normally of said longitudinal axis, whereby a force applied to said central portion in a first direction normal to said longitudinal axis will cause said linkage to move said driver means in a first axial direction and a force applied to said central portion in a second opposite direction normal to said longitudinal axis will cause said linkage to move said driver means in a second opposite axial direction, whereby said first and second tissue interacting means are caused to move from one to the other of said first open position and said second closed position depending on the direction of the normal force applied to said central portion;

said linkage being arranged so as that said mechanism is self-locking when said first and second tissue interacting means are in said second closed position;

said force-transmitting means comprising a movable member providing a shoulder on said inner shaft and a compression spring surrounding said inner shaft, said spring being captivated between and compressed to a selected loading by said shoulder and said driver means, said movable member being screwed onto said inner shaft so as to permit adjustment of the pre-loading of said compression spring.

33. A surgical instrument comprising:

an outer, hollow shaft having a longitudinal axis, a front end and a rear end;

an inner shaft co-axially disposed in said outer shaft for reciprocal relative movement, said inner shaft having a front end and a rear end and being longer than said outer shaft;

a jaw assembly attached to said front end of said first shaft, said jaw assembly comprising first and second tissue interacting jaws movable relative to one another between a first open position and a second closed position in response to axially directed changes in the relative positions of the said front ends of said outer and inner shafts;

a self-locking mechanism for changing the relative positions of said first and said second front ends lengthwise of said longitudinal axis, said mechanism comprising:

(A) driver means slidably mounted on said inner shaft substantially adjacent its said rear end;

(B) a toggle linkage for effecting relative axial movement of said outer and inner shafts and for locking said shafts in a selected position in which said jaws are held in said second closed position, said toggle linkage being adapted to receive a force applied substantially normally to said longitudinal axis and transmit said force to said driver means and said outer shaft so as to move said driver means relative to said outer shaft along the axis of said inner shaft, said toggle linkage comprising first and second members each having first and second ends, said first member having its first end pivotally attached to said rear end of said outer shaft at a first point eccentric to said inner shaft, and said second member having its first end pivotally connected to a portion of said first member that is spaced from said first end thereof, and its second end pivotally connected to said driver means at a second point eccentric to said inner shaft, the combined length of said first and second members being longer than the minimum axial separation between said first point and said second point when said first and second jaws are in said first open position and also when said first and second jaws are in said second closed position; and (C) force-transmitting means attached to said inner shaft and engageable with said driver means for transmitting an axial directed force from said driver means to said inner shaft in response to a force applied to said toggle linkage normally of said longitudinal axis, said force-transmitting means including a spring on said inner shaft for opposing movement of said driver means on said inner shaft in a direction that will cause said outer and inner shafts to undergo relative movement in the direction required to move said jaws into said second closed position, whereby (1) a force applied to said toggle linkage in a first direction normal to said longitudinal axis will cause said toggle linkage to move said driver means in a first axial direction and a force applied to said toggle linkage in a second opposite direction normal to said longitudinal axis will cause said toggle linkage to move said driver means in a second opposite axial direction, and (2) the relative positions of the front ends of said outer and inner shafts are changed and thereby said first and second jaws are caused to move from one to the other of said first open position and said second closed position according to the direction of the normal force applied to said toggle linkage;

said toggle linkage being movable into a self-locking condition as it forces said driver means to change the relative positions of the front ends of said inner and outer shafts in a direction that moves said first and second jaws into said second closed position.

34. An instrument according to claim 33 wherein said spring means urges said driver means along said inner shaft toward said front end of said inner shaft.

35. An instrument according to claim 33 wherein said spring means is a coiled compression spring surrounding said inner shaft, and further wherein said force-transmitting means comprises a shoulder on said inner shaft, with said spring being captivated between and compressed to a selected loading by said shoulder and said driver means.

36. An instrument according to claim 33 wherein said spring means is a compression spring surrounding said inner shaft, and further including adjustable means for adjusting the pre-loading of said spring, said adjustable means comprising a movable member screwed onto said inner shaft and engaging said spring.

37. An instrument according to claim 33 wherein when said first and second jaws are in said second closed position or clamped to tissue, a jaw closing force applied to said driver means by said linkage means which exceeds the pre-loading on said spring will cause said driver means to slide along said inner shaft so as to compress said spring, whereby substantially no further closing force is applied to said first and second jaws.

38. A surgical instrument comprising:

a hollow outer shaft having a proximal end and a distal end;

an inner shaft having a proximal end and a distal end, said inner shaft being located concentrically within said outer shaft and being movable axially relative to said outer shaft;

tissue interaction means attached to the distal end of said inner shaft, said tissue interacting means comprising first and second tissue-interacting members movable relative to one another between an open position and a closed position, and spring means biasing said first and second tissue-interacting members to remain in said open position, said inner and outer shafts being capable of telescoping movement whereby said distal ends of said shafts undergo relative movement between a first position wherein said distal end of said outer shaft embraces said tissue-interacting members and urges them into said closed position and a second position wherein said distal end of said outer shaft does not urge said tissue-interacting members into said closed position;

a manually operable mechanism for (a) effecting relative axial movement of said inner and outer shafts so as to move said tissue-interacting members from one to the other of said open and closed positions, and (b) controlling the relative positions of said first and said second distal ends, said manually operable mechanism comprising:

first pivot block means attached to said outer shaft adjacent the said proximal end thereof, said first pivot block means including a first projection extending from said outer shaft;

second pivot block means slidably mounted on said inner shaft substantially adjacent the said proximal end thereof, said second pivot block means including a second projection extending outwardly from said inner shaft;

a toggle linkage connecting said first and second pivot block means, said toggle linkage comprising first and second links each having a distal end and a proximal end, first pivot means pivotaly connecting the distal end of said first link to said first projection, second pivot means pivotally connection the proximal end of said second link to said second projection, and third pivot means pivotally connecting the distal end of said second link to said first link;

a spring surrounding said inner shaft and arranged so as to oppose movement of said second pivot block means along said inner shaft in a first axial direction corresponding to the direction of axial movement of said inner shaft relative to said outer shaft that will cause said second shaft to urge said tissue-interacting members into said closed position;

whereby (1) forces applied by said toggle linkage means to said second pivot block means in said first axial direction will cause movement of said inner shaft relative to said outer shaft so as to move said tissue-interacting members towards said closed position so long as said forces do not exceed the opposing force exerted by said spring, (2) when said tissue-interacting members are in said closed position or interacting with tissue, forces applied to said second pivot block means by said linkage means in said first axial direction which are larger than the opposing force exerted by said spring will cause said drive means to slide along said inner shaft without causing further relative movement of said inner shaft, and (3) said tissue-interacting members may be locked in said closed position by forcing said third pivot means to move from a point located radially outward of a line extending through said first and second pivot means to a point located radially inward of said line.

39. An instrument according to claim 38 wherein said inner shaft extends through said second pivot block means, a knob is mounted on the proximal end of said inner shaft, and said spring extends between said knob and said second pivot block means.

40. An instrument according to claim 38 wherein said inner shaft extends through said second pivot block means, a cap is mounted on said proximal end of said inner shaft, a shoulder is formed on said inner shaft, and said spring extends between said shoulder and said second pivot block means, said spring urging said second pivot block means away from said shoulder toward said cap.

41. A surgical instrument comprising:
a hollow outer shaft having a proximal end and a distal end;

an inner shaft having a proximal end and a distal end, said inner shaft being located concentrically within said outer shaft and being movable axially relative to said outer shaft;

tissue interaction means attached to the distal end of said inner shaft, said tissue interaction means comprising first and second tissue-interacting members movable relative to one another between an open position and a closed position, said first and second tissue-interacting members being biased to remain in said open position, said inner and outer shafts being capable of telescoping movement to an extent that said distal ends of said shafts undergo relative movement between a first position wherein said distal end of said outer shaft embraces said tissue-interacting members and urges them into said closed position and a second position wherein said distal end of said outer shaft does not urge said tissue-interacting members into said closed position;

a manually operable mechanism for (a) effecting telescoping movement of said inner and outer shafts so as to move said tissue-interacting members from one to the other of said open and closed positions, and (b) locking said shafts against movement when said distal ends are in said first position, said manually operable mechanism comprising:

first pivot block means secured to said outer shaft adjacent the said proximal end thereof, said first pivot block means including a pair of first projections extending outwardly from said outer shaft;

second pivot block means slidably mounted on said inner shaft with said first pivot block means disposed between said second pivot point block means and said distal ends of said shafts, said second pivot block means including a pair of second projections extending outwardly from said inner shafts;

a pair of like toggle linkages connecting said first and second pivot block means, each of said toggle linkages comprising first and second links each having a distal end and a proximal end, first pivot means pivotally connecting the distal end of said first link to one of said first projections, second pivot means pivotally connecting the distal end of said second link to said first link at a point spaced from the distal end of said first link; and a compression spring surrounding said inner shaft and arranged so as to bias said second pivot block against movement along said inner shaft in the same direction as the direction of relative movement of said inner shaft that is required to move said tissue-interacting members to said closed position;

whereby (1) forced applied by said toggle linkages to said second pivot block means in a first axial direction will cause said second pivot block means to move said inner shaft in said first axial direction relative to said outer shaft so as to move said tissue-interacting members towards said closed position, (2) when said tissue-interacting members are in said closed position or interacting with tissue, forces applied to said second pivot block means by said toggle linkages in said first axial direction which are larger than the axial force exerted by said spring on said second pivot block means will cause said second pivot block means to slide along said inner shaft in said first axial direction, and (b) said tissue-interacting members may be locked in its closed position by forcing said third pivot means inwardly toward said inner shaft across a line extending through said first and second pivot means.

42. An instrument according to claim 41 wherein one of the links of each toggle linkage is provided with a handle portion that can be grasped by a surgeon, whereby a surgeon can manually force said toggle linkages to effect relative axial movement between said inner and outer shafts.

43. An instrument according to claim 41 wherein said toggle linkages are diametrically opposed to one another.

44. An instrument according to claim 41 wherein said third pivot means is closer to said proximal end of said outer shaft than is said second pivot means.

45. An instrument according to claim 41 wherein said second pivot means is closer to said proximal end of said outer shaft than is said third pivot means.

46. An instrument according to claim 41 wherein said inner shaft is rotatable relative to said outer shaft and said first and second pivot block means.

47. In a surgical instrument of the type including a first shaft reciprocally disposed in a second shaft and means for interacting with tissue associated with one end of said shafts, said tissue-interacting means having an open position and a closed position, and means for causing said tissue-interacting means to move from said open position to said closed position and vice versa in response to relative axial movement of said shafts, the improvement comprising:

a self-locking mechanism for effecting said relative said movement of said shafts, said self-locking mechanism being associated with the other ends of said shafts and including a first pivot block, a second pivot block, biasing means, and linking means; said first pivot block being attached to said other end of said second shaft, said second pivot block being slidably mounted on said first shaft, said spring means being mounted on said first shaft, said spring means being mounted on said first shaft and bearing against said second pivot block so as to inhibit movement of said second pivot block along said first shaft in a first axial direction corresponding to the direction of axial movement of said first shaft in said second shaft which tends to move said tissue-interacting means to said closed position, and said toggle linkage means extending between said first pivot block and said second pivot block, said toggle linkage means having a maximum length longer than the minimum distance between said first pivot block and said second pivot block when said tissue-interacting means are in their closed and open positions, said linkage means normally being curved outwardly away from said shafts but being adapted to be moved by a force applied normally to the axis of said shafts to a position wherein it is curved inwardly and effectively locks said shafts against relative movement with said tissue-interacting means in said closed position.

* * * * *

UNITED STATES PATENT AND TRADEMARK OFFICE
CERTIFICATE OF CORRECTION

PATENT NO. : 5,308,357
DATED : May 3, 1994
INVENTOR(S) : Philip R. Lichtman

It is certified that error appears in the above-indentified patent and that said Letters Patent is hereby corrected as shown below:

Claim 1, column 14, line 8, delete the word "as";

Claim 5, column 14, line 27, the letter "t" should be changed to the word -- to --;

Claim 12, column 15, line 5, the numeral "12" should be changed to -- 11 --;

Claim 19, column 15, line 52, the word "wit" should be changed to -- with --;

Claim 19, column 16, line 21, after the word "direction", insert the words -- so as to move said --;

Claim 21, column 16, line 35, the word "mans" should be changed to -- means --;

Claim 38, column 20, line 63, the word "interacting" should be changed to -- interaction --;

UNITED STATES PATENT AND TRADEMARK OFFICE
CERTIFICATE OF CORRECTION

PATENT NO. : 5,308,357
DATED : May 3, 1994
INVENTOR(S) : Philip R. Lichtman

It is certified that error appears in the above-indentified patent and that said Letters Patent is hereby corrected as shown below:

Claim 38, column 21, line 29, the word "pivotaly" should be changed to -- pivotally --;

Claim 38, column 21, line 31, the word "connection" should be changed to -- connecting --;

Claim 41, column 22, line 48, the word "shafts" should be changed to -- shaft --;

Claim 47, column 24, line 7, delete the word "said" (first occurrence); and

Claim 47, column 24, lines 14 and 15, delete the words ", said spring means being mounted on said first shaft".

Signed and Sealed this

Thirteenth Day of September, 1994

Attest:

Attesting Officer

BRUCE LEHMAN

Commissioner of Patents and Trademarks